United States Patent
Warntjes (10) Patent No.: US 11,771,364 B2
(45) Date of Patent: Oct. 3, 2023

(54) METHOD AND SYSTEM FOR ESTIMATING BONE DENSITY

(71) Applicant: SyntheticMR AB (publ), Linköping (SE)

(72) Inventor: Marcel Warntjes, Linköping (SE)

(73) Assignee: SYNTHETICMR AB (PUBL), Linköping (SE)

( * ) Notice: Subject to any disclaimer, the term of this patent is extended or adjusted under 35 U.S.C. 154(b) by 242 days.

(21) Appl. No.: 17/159,379

(22) Filed: Jan. 27, 2021

(65) Prior Publication Data

US 2022/0233137 A1     Jul. 28, 2022

(51) Int. Cl.
*G06T 15/00*     (2011.01)
*A61B 5/00*     (2006.01)
(Continued)

(52) U.S. Cl.
CPC .......... *A61B 5/4509* (2013.01); *A61B 5/055* (2013.01); *A61B 5/7278* (2013.01); *A61B 5/7425* (2013.01); *G01R 33/5608* (2013.01); *G06T 7/11* (2017.01); *G06T 7/62* (2017.01); *G16H 30/40* (2018.01); *G16H 50/20* (2018.01); *A61B 5/459* (2013.01); *A61B 5/4566* (2013.01); *A61B 5/4571* (2013.01); *A61B 5/4585* (2013.01);
(Continued)

(58) Field of Classification Search
CPC .... G01R 33/448; G01R 33/50; G06T 7/0016; G06T 5/40; G06T 2207/30096; G06T 2207/10076; G06T 2207/10088; G06T 2207/30016; A61B 5/055; A61B 5/4842; A61B 5/7475
See application file for complete search history.

(56) References Cited

U.S. PATENT DOCUMENTS

| | | | |
|---|---|---|---|
| 2007/0055136 A1* | 3/2007 | Yamamoto | A61B 5/417 600/410 |
| 2010/0127704 A1* | 5/2010 | Warntjes | G01R 33/56 324/309 |

(Continued)

FOREIGN PATENT DOCUMENTS

CN     114469051 A *    5/2022

OTHER PUBLICATIONS

Du J, Bydder GM. Qualitative and quantitative ultrashort-TE MRI of cortical bone. NMR in biomedicine. May 2013;26(5):489-506.*

(Continued)

*Primary Examiner* — Phu K Nguyen
(74) *Attorney, Agent, or Firm* — Getech Law LLC; Jun Ye (57) ABSTRACT

A bone density estimating method, comprising: acquiring, by an MR scanning device, a magnetic resonance, MR, sequence of a body portion, wherein the MR sequence comprises quantitative information of the body portion; generating, by a processing circuit, an MR image of the body portion based on the MR sequence, wherein each voxel of the MR image represents a volume of the body portion; identifying, by the processing circuit, a part of the MR image representing a bone portion of the body portion; for a voxel of the identified part of the MR image, estimating a bone density of a volume of the bone portion represented by the voxel, based on a quantitative value of the voxel. The quantitative information of the body portion comprises a proton density.

21 Claims, 3 Drawing Sheets

(51) Int. Cl.
  *G06T 7/62* (2017.01)
  *G06T 7/11* (2017.01)
  *G16H 30/40* (2018.01)
  *G16H 50/20* (2018.01)
  *G01R 33/56* (2006.01)
  *A61B 5/055* (2006.01)

(52) U.S. Cl.
  CPC ....... *A61B 2576/02* (2013.01); *G06T 2200/24* (2013.01); *G06T 2207/10088* (2013.01); *G06T 2207/30008* (2013.01)

(56) References Cited

U.S. PATENT DOCUMENTS

| | | | | |
|---|---|---|---|---|
| 2013/0083987 | A1* | 4/2013 | Novak | G06T 7/174 382/131 |
| 2013/0315460 | A1* | 11/2013 | Warntjes | G06T 7/62 382/131 |
| 2017/0178319 | A1* | 6/2017 | Sugiura | G06F 3/04847 |
| 2017/0261584 | A1* | 9/2017 | James | G01R 33/4833 |
| 2021/0325499 | A1* | 10/2021 | Warntjes | G01R 33/5635 |
| 2022/0233137 | A1* | 7/2022 | Warntjes | G16H 50/30 |
| 2022/0273237 | A1* | 9/2022 | Alfredsson | G06T 7/0016 |

OTHER PUBLICATIONS

Ho KY, Hu HH, Keyak JH, Colletti PM, Powers CM. Measuring bone mineral density with fat-water MRI: comparison with computed tomography. Journal of Magnetic Resonance Imaging. Jan. 2013;37(1):237-42.*

Warntjes JB, Leinhard OD, West J, Lundberg P. Rapid magnetic resonance quantification on the brain: optimization for clinical usage. Magnetic Resonance in Medicine: An Official Journal of the International Society for Magnetic Resonance in Medicine. Aug. 2008;60(2):320-9.*

Chang HK, Hsu TW, Ku J, Ku J, Wu JC, Lirng JF, Hsu SM. Simple parameters of synthetic MRI for assessment of bone density in patients with spinal degenerative disease. Journal of Neurosurgery: Spine. Oct. 15, 2021;36(3):414-21.*

Wu HZ, Zhang XF, Han SM, Cao L, Wen JX, Wu WJ, Gao BL. Correlation of bone mineral density with Mri T2* values in quantitative analysis of lumbar osteoporosis. Archives of Osteoporosis. Dec. 2020; 15(1):1-7.*

Chang G, Rajapakse CS, Regatte RR, Babb J, Saxena A, Belmont HM, Honig S. 3 Tesla MRI detects deterioration in proximal femur microarchitecture and strength in long-term glucocorticoid users compared with controls. Journal of Magnetic Resonance Imaging. Dec. 2015;42(6):1489-96.*

Sollmann N, Löffler MT, Kronthaler S, Böhm C, Dieckmeyer M, Ruschke S, Kirschke JS, Carballido-Gamio J, Karampinos DC, Krug R, Baum T. MRI-based quantitative osteoporosis imaging at the spine and femur. Journal of Magnetic Resonance Imaging. Jul. 2021;54(1):12-35.*

Link TM, Kazakia G. Update on imaging-based measurement of bone mineral density and quality. Current rheumatology reports. May 2020;22(5):1-1.*

Hong J, Hipp JA, Mulkern RV, Jaramillo D, Snyder BD. Magnetic resonance imaging measurements of bone density and cross-sectional geometry. Calcified Tissue International. Jan. 1, 2000;66(1).*

Kühn JP, Hernando D, Meffert PJ, Reeder S, Hosten N, Laqua R, Steveling A, Ender S, Schröder H, Pillich DT. Proton-density fat fraction and simultaneous R2* estimation as an MRI tool for assessment of osteoporosis. European radiology. Dec. 2013;23:3432-9.*

J.B.M. Warntjes et al. "Rapid Magnetic Resonance Quantification on the Brain: Optimization for Clinical Usage", Magnetic Resonance in Medicine, vol. 60, 2008, pp. 320-329.

Glen M. Blake et al. "The Role of DXA Bone Density Scans in the Diagnosis and Treatment of Osteoporosis", Postgrad Med J, vol. 83, 2007, pp. 509-517.

Sungjoon Lee et al. "Correlation Between Bone Mineral Density Measured by Dual-Energy X-Ray Absorptiometry and Hounsfield Units Measured by Diagnostic CT in Lumbar Spine" J Korean Neurosurgical Society, vol. 54, 2013, pp. 384-389.

\* cited by examiner

METHOD AND SYSTEM FOR ESTIMATING BONE DENSITY

TECHNICAL FIELD

The present document relates to a method and system for estimating bone density. Particularly, the present document relates to a method and system for estimating and visualizing bone density.

BACKGROUND

A bone is a rigid organ that constitutes part of the vertebrate skeleton in animals. However, bones are not uniformly solid. A bone comprises osseous tissue being a hard tissue, and other soft tissues filled in its matrix.

Bone density, or bone mineral density (BMD), refers to an amount of bone mineral in bones. There is a statistical correlation between poor bone density and high probability of fracture. Fractures of the legs and pelvis due to falls have become a significant public health problem in many countries, especially in elderly women, which could lead to a high medical cost, inability to live independently, and even a risk of death.

Moreover, since bone density would affect screw pull-out strength, insertional torque and vertebral loading properties, good bone density is important to achieve optimal outcomes in surgeries, such as a spine surgery. Poor bone density increases a risk for vertebral fractures and implant failures.

Thus, bone density measurements not only can be used to screen people for osteopenia or osteoporosis and to identify those who might benefit from measures to improve bone strength, such as resistance exercises, but also are recommended before certain surgeries.

Bone density can be measured by Dual-Energy X-ray Absorptiometry (DXA or DEXA), which measures the bone mineral density using spectral imaging generated by two X-ray beams of different energy levels focused at bones. When soft tissue absorption is subtracted out, the BMD can be determined from the absorption of each beam by the bones. DEXA scan is the most widely used bone density measurement technology for diagnosing osteoporosis. The World Health Organization recognizes DEXA as a measure for effectiveness of targeted antifracture therapies, for example see Blake et al., *The role of DXA bone density scans in the diagnosis and treatment of osteoporosis*, Postgrad Med J 2007; 83:509-517.

However, even though DEXA can provide an accurate estimation of bone mineral density, due to accessibility, cost, and waiting time for such measurements, it is often omitted by the patients.

Thus, there is a need to provide a method and system for estimating bone density to improve the accessibility, reduce the cost, and shorten the waiting time for bone density measurements.

SUMMARY

It is an object of the present disclosure, to provide a new method and system for estimating bone density, which eliminates or alleviates at least some of the disadvantages of the prior art.

The invention is defined by the appended independent claims. Embodiments are set forth in the appended dependent claims, and in the following description and drawings.

According to a first aspect, there is provided a bone density estimating method, comprising: acquiring, by an MR scanning device, a magnetic resonance, MR, sequence of a body portion, wherein the MR sequence comprises quantitative information of the body portion; generating, by a processing circuit, an MR image of the body portion based on the MR sequence, wherein each voxel of the MR image represents a volume of the body portion; identifying, by the processing circuit, a part of the MR image representing a bone portion of the body portion; for a voxel of the identified part of the MR image, estimating a bone density of a volume of the bone portion represented by the voxel, based on a quantitative value of the voxel; wherein the quantitative information of the body portion comprises a proton density.

It is known that since MRI is not sensitive to bones, bones cannot contribute to the signals of MR images. Theoretically, it is difficult to measure bone density by MRI-based technologies. However, bones are not uniformly solid, wherein only the very surface of a bone is typically near-solid, whereas the internal part of the bone has a matrix structure filled by other tissues, e.g., bone marrow, which is a semi-solid tissue, blood vessels and water. When the bone density decreases, a partial volume filled by other tissues increases, and an amount of other tissues increases. Since it is known that bone marrow and water filled within the bones do contribute to the signals of the MRI images, MRI-based technologies can be used to analyze the bone marrow and water content within the bone. Consequently, it is possible to derive the remaining part except the bone marrow and water, i.e. a partial volume of the bone, which directly relates to bone density.

Compared to bone marrow and pure water, the observed signal of the solid bones in the MRI images is low caused by the presence of the non-signal-contributing bone fractions. Therefore, the absence of signal in an MR image can be interpreted as the presence of bone.

Even though the bone density estimated by MRI technologies may be not as accurate as DEXA, it can provide a good estimation of the bone density. Further, estimating bone density by MRI technologies is faster, less costly, and more accessible, which make it useful e.g., as, a preliminary screening. Estimating bone density by MRI technologies may be performed in combination with an already planned MRI examination.

A voxel is a volume element, used to represent a sub volume on a regularly spaced grid in a 3D space. Voxels are frequently used in the visualization and analysis of medical 3D images. Here, each voxel of an MR image represents a corresponding sub volume of the imaged portion. Each voxel of the MR image has a quantitative value, e.g., the observable proton density, PD, representing a quantitative property of the tissues of the corresponding tiny volume.

A pixel is an element used to represent a tiny 2D portion in a 2D image. The 3D imaged portion may be sliced into a stack of slices each having a thickness. A voxel may be considered to correspond to a pixel for a given slice thickness. In other words, a voxel can be considered as a volumetric pixel for the given slice thickness.

The step of estimating a bone density may comprise calculating a bone partial volume of the volume of the bone portion represented by the voxel, based on the quantitative value of the voxel; wherein the bone partial volume is a value represents a percentage of a bone tissue of a portion.

The bone tissue may refer to a bone fraction excluding any other tissues, such as the bone marrow, the blood vessels, and water, etc. Thus, for any tissue, the bone partial volume may be a percentage of bone fractions within the tissue. That is, a higher bone partial volume means that this tissue has fewer other tissues, such as the bone marrow, the vessels and the water. Consequently, the bone partial volume can be used to represent the bone density. The higher the bone partial volume, the higher the bone density. The lower the bone partial volume, the lower the bone density.

The bone partial volume may be calculated as (100−(PD/A)) %, wherein PD is a proton density of the voxel, A is a first scaling factor, preferably in a range of 1.0 to 1.4.

Using quantitative MRI, it is possible to quantify the proton density (PD) of all MR-visible tissues of an imaged portion. Pure water is defined as having a PD % of 100%. That is, a tissue comprising only water has a PD % of 100%, and a tissue comprising only bone tissues without any water has a PD % of 0%. A tissue of a mixture of water and bone tissues results in a PD in the range 0-100, where a partial volume of the bone fractions of the tissue corresponds to 1-PD %, i.e. (100-PD) %. For MR acquisitions, bones do not provide a measurable signal, whereas water and bone marrow do. Hence, the observable PD intensity originates from the water and the bone marrow of the tissue, not from the bone fractions of the tissue.

The bone marrow has a higher density of protons per volume than water, which typically exhibits a PD % of 140%. That is, a tissue comprising only bone marrow has an observable PD % of 140%, and a tissue comprising only bone without any water has an observable PD % of 0%. Thus, a tissue of a mixture of the bone marrow and bone tissues results in a PD in the range 0-140. Consequently, the scaling factor A can be used to refine the estimation, to account for the contribution of water and bone marrow.

The method may comprise converting the calculated bone partial volume to a T-score value.

Although the bone partial volume can be used to represent the bone density, it is not a standard measure. For example, DEXA uses T-score as a standard measure of bone density, e.g., for screening for osteoporosis. A T-score tells a bone mineral density in comparison to a young adult of the same gender with peak bone mineral density. A T-score of −1.0 and above indicates normal, while a T-score between −1.0 and −2.5 indicates a low bone density is, and a T-score of −2.5 and lower indicates osteoporosis.

It is advantageous to convert the calculated bone partial volume to a well-known T-score value, which can be easily understood and used for comparison.

Based on correlation values provided by e.g., Lee et al. *"Correlation between Bone Mineral Density Measured by Dual-Energy X-Ray Absorptiometry and Hounsfield Units Measured by Diagnostic CT in Lumbar Spine"*, JKNS 54:384-389, 2013, a bone partial volume and a T-score value may have a corresponding relationship. That is, the calculated bone partial volume may be converted to a T-score value.

For example, it is assumed that a 45% bone partial volume corresponds to a T-score value of 0. And a 25% bone partial volume corresponds to a T-score of −4. However, these corresponding relationships are only estimations based on literatures. The corresponding relationship of bone partial volumes and T-scores may be changed or refined based on further measurements.

The step of estimating a bone density may comprise calculating a T-score value of the volume of the bone portion represented by the voxel, based on the quantitative value of the voxel.

Instead of converting the bone partial volume to a T-score value, it is possible to directedly calculate the T-score value based on the quantitative value of the voxel.

The T-score value may be calculated as T-score value=E−D*PD %, wherein PD is a proton density of the voxel, E is an offset, and D is a second scaling factor.

The offset E may be 8.0 and the second scaling factor D may equal to 11.4. For example, a tissue comprises only the bone marrow and the bone tissues. When the tissue has a PD % of 70%, its calculated T-score value would be 0 (i.e. normal). When the tissue has a PD % of 105%, its calculated T-score value would be −4 (i.e. osteoporosis).

The quantitative information of the body portion may further comprise at least one of: a longitudinal relaxation rate R1, and a longitudinal relaxation time T1. The longitudinal relaxation rate R1 is the reciprocal of the longitudinal relaxation time T1, i.e. R1=1/T1. The longitudinal relaxation time T1 is typically measured in milliseconds (ms) or seconds (s). The longitudinal relaxation rate R1 is measured in units of $ms^{-1}$ or $s^{-1}$.

The method may comprise calculating the first scaling factor A by a formula A=B+C*R1, or A=B+C/T1, wherein R1 is a longitudinal relaxation rate of the voxel, T1 is a longitudinal relaxation time of the voxel, and B and C are two constants such that the first scaling factor A is in a range of 1.0 to 1.4.

When it is assumed that a bone portion consists only the bone fractions and the bone marrow, the first scaling factor A may be determined to be 1.4, as it is known that the bone marrow has a PD % of 140%. The bone partial volume can be calculated as (100−(PD/1.4)) %.

However, besides the bone fractions and the bone marrow, the bone portion may comprise water (for example edema), which would lead to a lower PD value of the bone portion, and hence an overestimation of bone density.

Thus, the first scaling factor A may be refined to provide a more accurate estimation of the bone density.

Since it is known that the bone marrow and water have different longitudinal relaxation rates R1, it is possible to separate the bone marrow and water of a tissue, based on the longitudinal relaxation rate R1 of a voxel of the MR image representing the tissue.

Typically, water has a R1 smaller than 0.4 $s^{-1}$, whereas the bone marrow has a R1 larger than 2 $s^{-1}$. Thus, the first scaling factor A for calculating the bone partial volume of a tissue may be determined based on the R1 or T1 of a voxel of the MR image representing the tissue, by the formula A=B+C*R1, or A=B+C/T1.

The first scaling factor A can be represented as a function of R1 or T1, such that the first scaling factor A is 1.0 when R1 equals to 0.4 $s^{-1}$ (i.e. there is only water, and no bone marrow presents within the tissue), and 1.4 when R1 equals to 2 $s^{-1}$ (i.e. there is only bone marrow, and no water presents within the tissue). The allowed range of the first scaling factor A can be limited to [1.0-1.4], to prevent extreme values. The constant B may be 0.9, and the constant C may be 0.25.

Thus, when the quantitative information of the body portion comprises PD and at least one of R1 and T1, the bone partial volume can be calculated as (100−PD/(0.9+0.25*R1) %.

The method may comprise calculating the second scaling factor D by a formula D=16/(B+C*R1), or D=16/(B+C/T1), wherein R1 is a longitudinal relaxation rate of the voxel, T1 is a longitudinal relaxation time of the voxel, and B and C are two constants.

Analogously, the second scaling factor D may be refined based on the R1 or T1 of a voxel to provide a more accurate estimation of the bone density. The constant B may be 0.9, and the constant C may be 0.25. Consequently, the T-score value may be calculated by the following formulae $$T\text{-score value} = 8.0 - 16 * PD \% / (0.9 + 0.25 * R1), \text{ or}$$

$$T\text{-score value} = 8.0 - 16 * PD \% / (0.9 + 0.25 * 1/T1).$$

The method may comprise repeating the step of estimating a bone density for each voxel of the identified part of the MR image.

The method may comprise: generating a bone density image for visualizing the estimated bone density for each voxel of the identified part of the MR image; wherein each voxel of the bone density image visualizes a bone density of its corresponding voxel of the identified part of the MR image; and wherein different bone densities are displayed differently in the bone density image.

The bone density image may have a same shape as that of the identified part of the MR image, such that the voxels of the bone density image and the voxels of the identified part of the MR image have a one-to-one relationship.

Different bone densities may be displayed in different colors or different intensities in the bone density image. Different colors or intensities may facilitate visualizing the bone density.

For example, one voxel of the bone density image displayed in a darker color, e.g., in black, may indicate that the tissue represented by its corresponding voxel of the identified part of the MR image having a low bone density. Another voxel of the bone density image displayed in a brighter color, e.g., in white or grey, may indicate that the tissue represented by its corresponding voxel of the identified part of the MR image having a high bone density.

The term "intensity", also known as "signal intensity", in the field of MR may refer to a shade of grey of a voxel in an MRI image. Generally, a high intensity means it looks "white" in the MRI image, an intermediate intensity means it looks "grey" in the MRI image, and a low intensity means it looks "black" in the MRI image.

The method may comprise displaying, by a user interface, the bone density image.

The method may comprise displaying the identified part of the MR image, the MR image or a different image representing an anatomy of the body portion or the bone portion as a background image; and displaying the bone density image as an overlay to the background image.

Displaying the background image showing an anatomy and using the bone density image as an overlay may facilitate a user correlating the visualized bone density to its anatomy.

The body portion may comprise a plurality of vertebrae of a spine, and at least one vertebra of the plurality of vertebrae does not intersect a sagittal plane. The method may comprise generating a partial sagittal MR image for each of the plurality of vertebrae based on the MR sequence; combining partial MR sagittal images into a sagittal reformat MR image, as the MR image of the body portion based on the MR sequence; wherein the plurality of vertebrae is visualized in the sagittal reformat MR image.

In anatomy, the sagittal plane, or longitudinal plane, is an anatomical plane which divides the body into right and left parts. For a normal person, all the vertebrae of a spine should be substantially centered to the sagittal plane.

In other words, all the vertebrae of the spine of the normal person would intersect the sagittal plane. However, for a patient suffering from scoliosis, the spine may be bent in the left-hand, and/or right-hand direction. For such patients, some of the vertebrae may not cross the sagittal plane. That is, some of the vertebrae may not be visible in the sagittal MR image. Thus, it is impossible to estimate the bone density of all the vertebrae based on one sagittal MR image.

Instead, it is possible to e.g., find a center line of the spine, and for each vertebra determine a partial sagittal MR image close to the center line of the spine, and combine these partial sagittal images to a single sagittal reformat MR image. Such a sagittal reformat MR image comprise PD and/or R1 values of all the vertebrae, which can be used to estimate bone density for the entire spine.

The method may comprise calculating an average bone density of a region of interest of the identified part of the MR image.

The region of interest may be a vertebra, such that the average bone density of the vertebra of the spine may be calculated. When the region of interest is the whole bone portion, the average bone density of the whole bone portion may be calculated.

The method may comprise displaying the calculated average bone density value.

The body portion may comprise any of a spinal bone, a hip bone, a leg bone, an ankle, a long bone, a wrist, a knee and a skull.

The step of identifying a part of the MR image may comprise segmenting, by the processing circuit, the part of the MR image representing the bone portion.

According to a second aspect, there is provided a bone density estimating system, comprising: an MR scanning device, configured to acquire a magnetic resonance, MR, sequence of a body portion, wherein the MR sequence comprises quantitative information of the body portion; a processing circuit configured to: generate an MR image of the body portion based on the MR sequence, wherein each voxel of the MR image represents a volume of the body portion; identify a part of the MR image representing a bone portion of the body portion; for a voxel of the identified part of the MR image, estimate a bone density of a volume of the bone portion represented by the voxel, based on a quantitative value of the voxel; wherein the quantitative information of the body portion comprises a proton density.

The system may further comprise a user interface configured to display images. The user interface may be configured to output information, such as texts, sounds, images, etc.

The user interface may be configured to receive input, e.g., a command, from a terminal or an input device via a wire or wirelessly. The user interface may be configured to receive input from a user.

According to a third aspect, there is provided a non-transitory computer readable recording medium having computer readable program code recorded thereon which when executed on a device having processing capability is configured to perform the method.

BRIEF DESCRIPTION OF THE DRAWINGS

FIG. 3b is a coronal MR image of the spine portion of FIG. 3a.

DESCRIPTION OF EMBODIMENTS

The present invention will now be described more fully hereinafter with reference to the accompanying drawings, in which currently preferred embodiments of the invention are shown.

Figure 5:
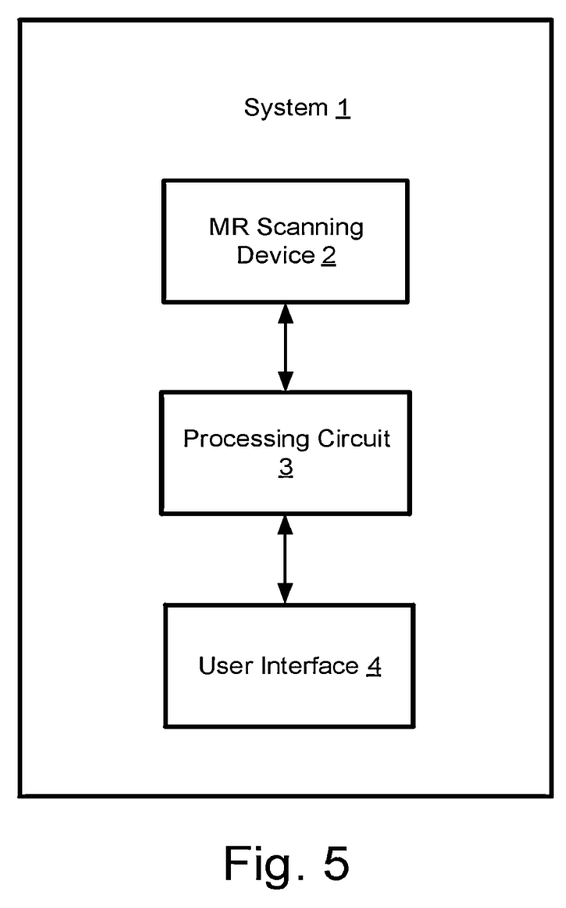
FIG. 5 is an example of a schematic block diagram of a bone density estimating system.

In connection with FIG. 5, the system 1 for estimating bone density will be discussed in more detail.

The system 1 comprises an MR scanning device 2. The MR scanning device 2 may be configured to acquire an MR sequence of a body portion comprising bones.

A typical MR scanning device may be an MR scanner, which comprises a large, powerful magnet, and can send signals to, e.g., a body portion of a patient. The returning signals can be detected and converted into images of the body portion by a computer device. The images can be obtained in multiple planes (axial, sagittal, coronal, or oblique) without repositioning the patient.

The MRI techniques are generally based on relaxation properties of excited hydrogen nuclei (protons) of an object under test. When the object to be imaged is placed in a powerful, uniform magnetic field of the MR scanner, the spins of the atomic nuclei of water in the object with non-integer spin numbers within the object all align either parallel or anti-parallel to the magnetic field. From an MR acquisition, several physical properties of the object under test can be determined. And an image can be reconstructed based on an acquired magnetic resonance sequence generated with the excitation.

Proton density refers to a concentration of protons in a tissue, wherein the protons are the hydrogen nuclei that resonate and give rise to the nuclear magnetic resonance signal. Since most visible tissue protons are resident in water, it is often seen as looking at a water content. The proton density of a tissue usually refers to the concentration of protons in the tissue, relative to that in the same volume of water at the same temperature.

The following time constants involved in the relaxation processes, which establish equilibrium following RF excitation, should be introduced in order to understand the MRI techniques. A nuclear magnetic resonance signal is affected by two simultaneous relaxation processes. The loss of coherence of the spin system attenuates the MRI signal with a time constant called a transverse relaxation time (T2). Concurrently, the magnetization vector slowly relaxes towards its equilibrium orientation that is parallel to the magnetic field by a time constant called longitudinal relaxation time (T1). A longitudinal relaxation rate R1 is the reciprocal of the longitudinal relaxation time T1 (R1=1/T1). A transverse relaxation rate R2 is the reciprocal of the transverse relaxation time T2 (R2=1/T2). The relaxation times T1 and T2 are typically measured in milliseconds (ms) or seconds (s). The corresponding relaxation rates R1 and R2 are therefore measured in units of $ms^{-1}$ or $s^{-1}$.

Normally, an acquired MRI sequence can result in images of the same anatomical section under different contrasts, such as T1-weighted, T2-weighted and PD-weighted images. The MRI techniques relies on differences in relaxation properties and proton density of the imaged tissue to display the different tissues with contrast, e.g., in different signal intensities or different colors, in the resulting MRI images. The contrast in MR images originates from the fact that different tissues have, in general, different R1 and R2 relaxation rates, and different proton densities. For example, Warntjes et al. *Magn Reson Med.* 2008; 60:320-9 teaches that these physical properties, e.g., R1 and R2 relaxation rates and PD, can be acquired by performing a single MR acquisition, to provide quantitative values of the imaged portion.

The system 1 comprises a processing circuit 3, configured to carry out overall control of functions and operations of the system 1. The processing circuit 3 may include a processor, such as a central processing unit (CPU), microcontroller, or microprocessor.

The system 1 may comprise a memory. The processing circuit 3 may be configured to execute program codes stored in the memory, in order to carry out functions and operations of the system 1.

The memory may be one or more of a buffer, a flash memory, a hard drive, a removable medium, a volatile memory, a non-volatile memory, a random access memory (RAM), or another suitable device. In a typical arrangement, the memory may include a non-volatile memory for long term data storage and a volatile memory that functions as system memory for the system 1. The memory may exchange data with the processing circuit over a data bus. Accompanying control lines and an address bus between the memory and the processing circuit also may be present.

Functions and operations of the system 1 may be embodied in the form of executable logic routines (e.g., lines of code, software programs, etc.) that are stored on a non-transitory computer readable medium (e.g., the memory) of the system 1 and are executed by the processing circuit 3. Furthermore, the functions and operations of the system 1 may be a stand-alone software application or form a part of a software application that carries out additional tasks related to the system 1. The described functions and operations may be considered a method that the corresponding device is configured to carry out. Also, while the described functions and operations may be implemented in software, such functionality may as well be carried out via dedicated hardware or firmware, or some combination of hardware, firmware and/or software.

The system 1 may comprise a user interface 4. The user interface 4 may be configured to output data and information, e.g., the MR image of the body portion, calculated bone partial volumes, calculated T-score values, bone density images, etc. The user interface 4 may be configured to receive data and information, such as a command, from one or several input devices. The input device may be a computer mouse, a keyboard, a track ball, a touch screen, or any other input device. The user interface 4 may send the received data and information to the processing circuit 3 for further processing.

In connection with FIGS. 1a-1c and 2a-2c, the bone density estimating method will be discussed in more detail.

Figure 1A:
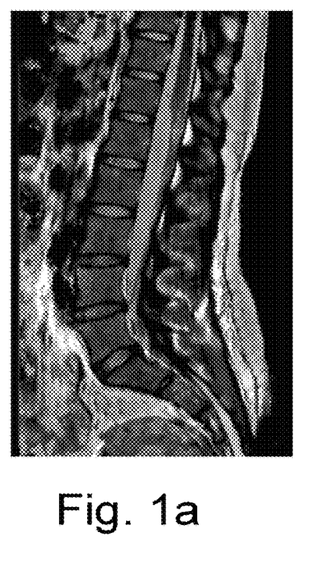
FIGS. 1a-1b are MR images of a spine portion of a forty-five years old female.
Figure 2A:
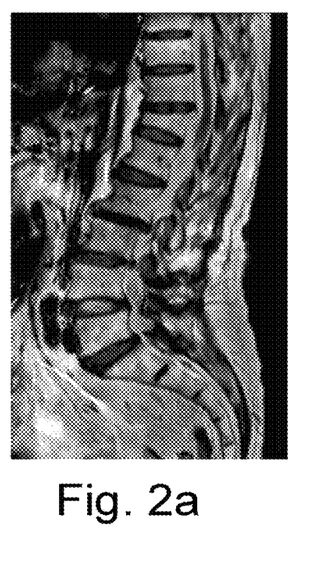
FIGS. 2a-2b are MR images of a spine portion of an eighty-six years old female.

FIGS. 1a and 2a are MR images of a spine portion of a forty-five years old female and of an eighty-six years old female, respectively. The forty-five years old female is healthy, and the eighty-six years old female has an old spinal fracture and suffers from osteoporosis. FIGS. 1a and 2a are sagittal images. In anatomy, the sagittal plane is an anatomical plane which divides the body into right and left parts. For a normal person, all the vertebrae of a spine should be substantially centered to the sagittal plane. Thus, the sagittal images, e.g., FIGS. 1a and 2a, should be sufficient for visualizing all the vertebrae.

It is known that the acquired MR sequence has already defined the characteristics of different tissues, including the water and the bone marrow, in terms of signal behaviors of one or more images, e.g., FIGS. 1a and 2a.

The MR sequence comprises quantitative information of the portion. The quantitative information of the portion may comprise a Proton Density, PD, and a longitudinal relaxation rate R1, or a longitudinal relaxation time T1.

The quantitative value for each voxel in FIGS. 1a and 2a is PD, which describe the signal behavior of the slice resulted from the MR sequence. Thus, the MR images of FIGS. 1a and 2a are also known as PD maps. Both FIGS. 1a and 2a are obtained on a scale of 50-150%.

The quantitative value of any voxel of the MR image may be used to determine the tissue(s) of the tiny volume represented by the voxel. That is, it is possible to tell whether a voxel represents bone fractions, water, bone marrow or a mixture of them, based on the quantitative value of this voxel.

Figure 1B:
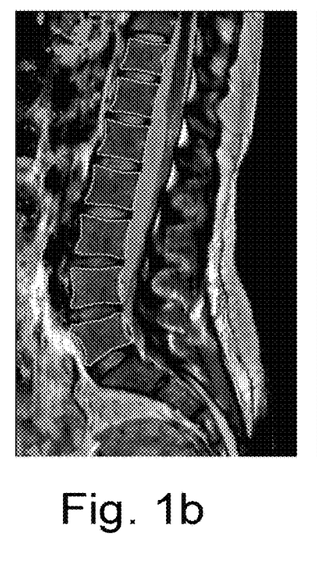
Figure 2B:
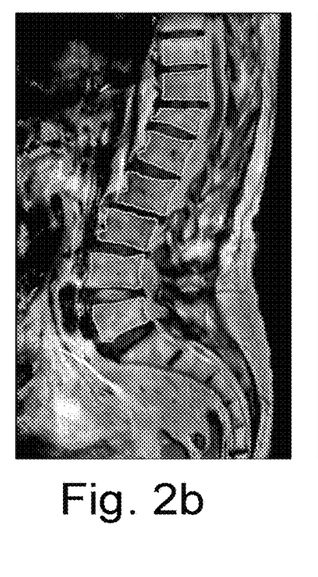

The parts of the MR images of FIGS. 1a and 2a representing the spine bones may be identified by known methods, e.g. segmenting. In FIGS. 1b and 2b, the identified parts of the MR images representing the spine bones are marked by grey solid lines. The spine bones segmentation can be achieved based on any of their relative positions in a body with respect to the spinal canal, their shapes and the PD values of the voxels of the PD maps. Typically, in the PD maps, the spinal canal is very bright (hyperintense), the spinal vertebrae are grey, and the intervertebral disks have dark outlines and brighter centers.

FIGS. 1b and 2b are examples illustrating one way of visualizing the identified parts of the MR images representing the bones. The identified parts may be marked in different ways as long as they are identifiable from other parts of the MR image. For example, the identified parts may be marked by a dotted line, or an overlay.

It is known that MRI is not sensitive to bones and therefore bones will not contribute to the signal in MR images. However, using quantitative MRI, it is possible to quantify the proton density of all MR-visible tissues of an imaged portion. Pure water is defined as having a PD % of 100%. That is, a tissue comprising only water has a PD % of 100% (i.e. PD=100), and a tissue comprising only bone fractions without any water has a PD % of 0% (i.e. PD=0). A tissue of a mixture of water and bone fractions may result in a PD in the range 0-100. A bone partial volume referring to a percentage of a bone fraction of a tissue may correspond to (100-PD) %. In other words, a bone partial volume of a tissue comprising only water is 0%, and a bone partial volume of a tissue comprising only bone fractions without water is 100%.

In FIGS. 1b and 2b, each voxel of the identified parts of the MR images represents a tiny volume of the spine bones, and each voxel has a PD value showing characteristics of the volume of the spine bones it represents. A bone partial volume can be calculated based on the quantitative value of the voxel. The calculated bone partial volume may represent an estimated bone density of that volume.

Besides water, the bone may comprise bone marrow, which has a higher density of protons per volume than water, and typically exhibits a PD % of 140%. That is, a tissue comprising only bone marrow has an observable PD % of 140%, and a tissue comprising only bone fractions without any bone marrow has an observable PD % of 0%. Thus, a tissue of a mixture of the bone marrow and bone fractions may result in a PD in the range of 0-140. For each voxel of the identified parts of the MR images representing the bones, a bone partial volume of a tissue that the voxel represents may be calculated by the following formula (1):

$$\text{Bone Partial Volume} = (100 - (PD/A))\%, \quad \text{formula (1)}$$

wherein PD is an observable proton density of the voxel, and A is a first scaling factor.

The scaling factor A may refine the calculation of the bone partial volume. Assuming that a bone portion comprises only any of the bone fractions, the water, and the bone marrow, the scaling factor A may be in a range of 1.0 to 1.4, corresponding to the PD % of pure water and of the bone marrow, respectively.

Although the calculated bone partial volume can be used to represent the bone density, it is not a widely used standard measure.

DEXA uses T-score as a standard measure of bone density, e.g., for screening for osteoporosis. A T-score tells a patient what his bone mineral density is in comparison to a young adult of a same gender with peak bone mineral density. A normal person has a T score being −1.0 or above, a person with a low bone density has a T score between −1.0 and −2.5, and a person suffering from osteoporosis has a T score being −2.5 or lower.

The calculated bone partial volume can be converted to a T-score value. For each voxel of the identified parts of the MR images, the calculated bone partial volume may be converted to a T-score value. An average T-score value of a region of interest of the MR image may be calculated by averaging the T-score values of all the voxels of the region of interest.

Alternatively, an average bone partial volume of a region of interest of an MR image may be calculated first, e.g., by averaging the calculated bone partial volume of all the voxels of the region of interest. Then, the average bone partial volume may be converted to an average T-score value of the region of interest.

Since the T-score is well known, the converted T-score value can be easily used, e.g., for comparing with bone densities measured by other methods, such as DEXA.

For each voxel of the identified parts of the MR images, a T-score value of a volume of the bone portion represented by the voxel may be calculated based on the quantitative value of the voxel. In other words, instead of converting the calculated bone partial volume to a T-score value, it is possible to directedly calculate the T-score value based on the quantitative value of the voxel.

The T-score value may be calculated by the following formula (2):

$$T\text{-score value} = E - D * PD\ \%; \quad \text{formula (2)}$$

wherein PD is an observable proton density of the voxel, D is a second scaling factor, and E is an offset. The scaling factor D may equal to 11.4. The offset E may equal to 8.0.

For example, a normal bone portion, comprising only the bone fractions and little bone marrow, has a PD % of 70%, it would give a T-score value of 0, indicating it is normal. If a bone portion of a low density, comprising only the bone fractions and more bone marrow, has a PD % of 105%, it would give a T-score value of −4, indicating osteoporosis.

In reality, since the bone portion normally comprises bone marrow, but may have in pathological cases infiltration of water (edema), relying only on the PD values may lead to an overestimation or underestimation of bone density as it is difficult to determine the first scaling factor A of the formula (1).

This may be improved by also measuring additional characteristics of the imaged tissue, to separate the water from the bone marrow.

The additional characteristics may be at least one of: a longitudinal relaxation rate R1, and a longitudinal relaxation time T1. An R1 relaxation map of the imaged body portion may be generated. Typically, the water has a R1 smaller than 0.4 s$^{-1}$, whereas the bone marrow has a R1 larger than 2 s$^{-1}$. Thus, the first scaling factor A can be represented as a function of R1, such that the scaling factor A is 1.0 when R1 equals to 0.4 s$^{-1}$ (when there is only water and no bone marrow presents within the volume) and the first scaling factor A is 1.4 when R1 equals to 2 s$^{-1}$ (when there is only bone marrow and no water presents within the volume).

Thus, the first scaling factor A of the formula (1) may be calculated based on the R1 of the voxel, by the following formula (3):

$$A=B+C*R1, \quad \text{formula (3)}$$

wherein R1 is a longitudinal relaxation rate of the voxel, and B and C are two constants.

To prevent extreme values, the constants B and C are selected in a way such that the first scaling factor A is in a range of 1.0 to 1.4. For example, the constant B may be 0.9, and the constant C may be 0.25.

Since a longitudinal relaxation time T1 of the voxel equals to 1/R1, the formula (3) may be rewrite into the following formula (4):

$$A=B+C/T1, \quad \text{formula (4)}$$

wherein T1 is a longitudinal relaxation time of the voxel.

Analogously, the second scaling factor D of formula (2) can be calculated based on the R1 of the voxel, by the following formulae (5) and (6):

$$D=16/(B+C*R1), \text{ or} \quad \text{formula (5)}$$

$$D=16/(B+C/T1). \quad \text{formula (6)}$$

With any of the above formulae (1)-(6), a bone partial volume and/or a T-score value, each representing an estimation of bone density, for each voxel of the identified parts of the MR images of FIGS. 1b and 2b representing the bone portions, can be determined. Based on the estimated bone partial volume and/or a T-score value for each voxel of the identified parts of the MR image, a bone density image for visualizing the estimated bone density may be generated.

Figure 1C:
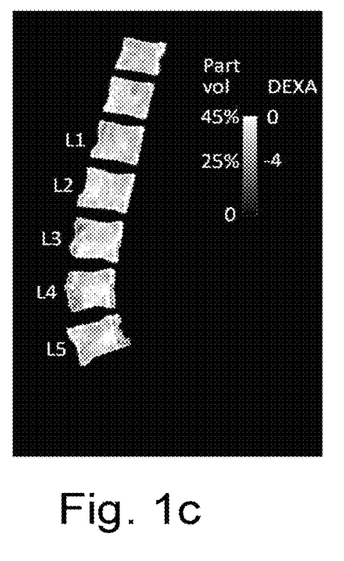
FIG. 1c is an image visualizing bone density.
Figure 2C:
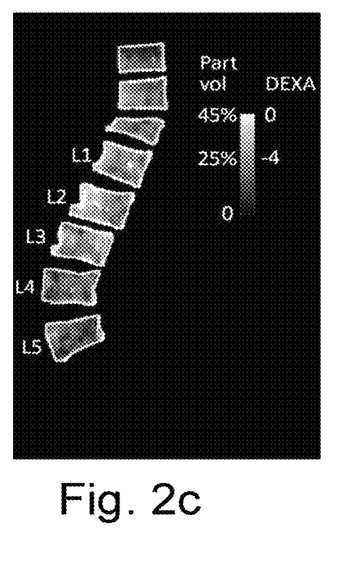
FIG. 2c is an image visualizing bone density.

FIGS. 1c and 2c are two examples of bone density images for visualizing the estimated bone density for each voxel of the identified part of the MR image. The visualized bone densities in FIGS. 1c and 2c are calculated based on both PD and R1 of the quantitative MR sequence.

The bone density image may comprise voxels corresponding to the voxels of the identified part of the MR image in a one-to-one corresponding relationship, such that the bone density image has a same shape as that of the identified parts of the MR image. For example, the shape of FIG. 1c corresponds to the identified parts in FIG. 1b.

Each voxel of the bone density image visualizes an estimation of bone density, i.e. a bone partial volume and/or a T-score value, calculated based on the quantitative value of its corresponding voxel of the identified part of the MR image. Different bone densities may be displayed differently in the bone density image.

In FIGS. 1c and 2c, a scale bar is provided as a reference for interpreting the visualized bone densities, including both bone partial volumes (indicated as "Part vol" in FIGS. 1c and 2c) and T-score values (indicated as "DEXA" in FIGS. 1c and 2c). The higher intensity (brighter) the voxel, the higher its T-score values, and the higher its bone partial volumes. In this example, it is assumed that a 25-45% bone partial volume corresponds to T-scores −4 to 0.

In FIG. 1c, all voxels have a high intensity, which correspond to about a bone partial volume of 40-45%, indicating a high bone density (T-scores>−1). In comparison, the PD values of the vertebrae in FIG. 2a are much higher and all voxels in FIG. 2c have a lower intensity, which correspond to a bone partial volume of about 15-25%, confirming that the patient suffers from osteoporosis (T-scores<−2.5).

The bone density image may comprise a background image. The background image may be an anatomical image showing an anatomy of the body portion or the bone portion. The background image may be the MR image of the body portion. The background image may be generated based on the MR sequence of the portion, or based on a different MR sequence of the portion. The bone density image may be displayed as an overlay to the background image. The bone density image may be displayed side by side with the background image. Providing the background image may facilitate correlating the bone densities to the anatomy.

For facilitating interpretation, labels of the spine bones can be added, for example L1-L5 for the lumbar spine are added in FIGS. 1c and 2c.

A plurality of bone density images representing a plurality of slices may be generated and displayed.

An average bone partial volume and/or an average T-score value can be calculated for a region of interest, such as a vertebra. An average bone partial volume and/or an average T-score value for all the voxels of the bone density image may be calculated for providing a mean bone density, or a mean T-score value, of the identified part of the MR image.

Thus, the bone density of one specific bone or a region of interest can be represented by one value, instead of an image, which can further simplify the visualization of the bone density. Consequently, a set of values representing the bone density of different bones can be used to visualize the bone density of the different bones. The set of values can be used to compare a patient with a healthy peer for a quick analysis. It can also be used to compare between a patient group and its healthy peers. The set of values may change over time and from scan to scan, which can be used to monitor bone density changes of a patient.

The set of values may be displayed, e.g., in the form of a table, for recording and/or reporting.

Scoliosis is a medical condition in which a person's spine has a sideways curve, typically in an "S" or "C" shape. Patients suffering from scoliosis would typically have a spine bent in the left-hand, and/or right-hand direction. In other words, all the vertebrae of the spine of a normal person would intersect the sagittal plane. However, for patients suffering from scoliosis, in extreme situations, some of the vertebrae may not intersect the sagittal plane. That is, some of the vertebrae may not be visible in the MR images of the sagittal slice. For such patients, it is impossible to generate an MR image of a single sagittal slice showing all vertebrae.

Figure 3A:
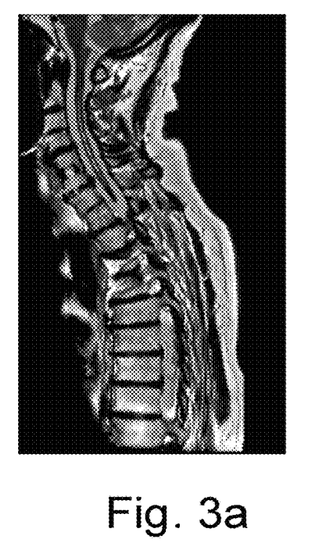
FIG. 3a is an MR image of a spine portion of a person.

FIG. 3a is a PD map of a sagittal slice from a patient suffering from scoliosis. It is difficult to estimate bone density for the spine bones based on the PD map of FIG. 3a, for the above-mentioned reasons.

Figure 3B:
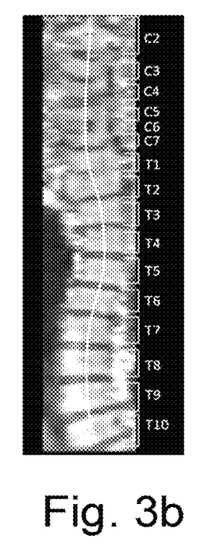

FIG. 3b is a MR image of a coronal slice of the same patient. A coronal plane, also known as a frontal plane, is a vertical plane that divides the body into ventral and dorsal (belly and back) parts. In FIG. 3b, labels C2-C7 are added for marking the cervical spine, and T1-T12 are added for marking the thoracic spine. Further, a center line connecting a center of the spine is added in FIG. 3b, which clearly shows that the spine has an "S" shape.

Figure 3C:
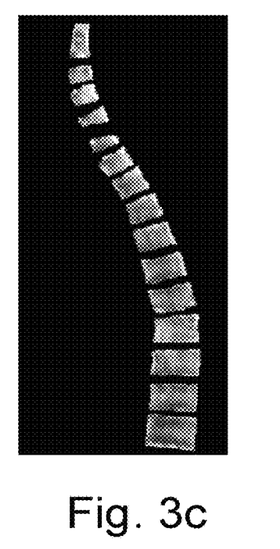
FIG. 3c is an image visualizing bone density.

A plurality of partial PD maps, each visualizing a sagittal slice of one part of the spine, e.g., one vertebra, may be generated. For example, it is possible to find the center line of the spine in FIG. 3b. A partial PD map may be based on a sagittal slice closest to the center line. Then, the plurality of partial PD maps may be combined together to create a sagittal reformat PD map of the spine, such that each part of the spine is visualized in the sagittal reformat PD map. Such sagittal reformat PD map can visualize the entire spine in a single image. Consequently, based on the sagittal reformat PD map, the same method can be used for estimating bond density. FIG. 3c is a bone density image generated based on such sagittal reformat PD map.

Comparing with FIG. 3a, FIG. 3c clearly visualized the bone density of the spine parts not equally visible in FIG. 3a.

Figure 4A:
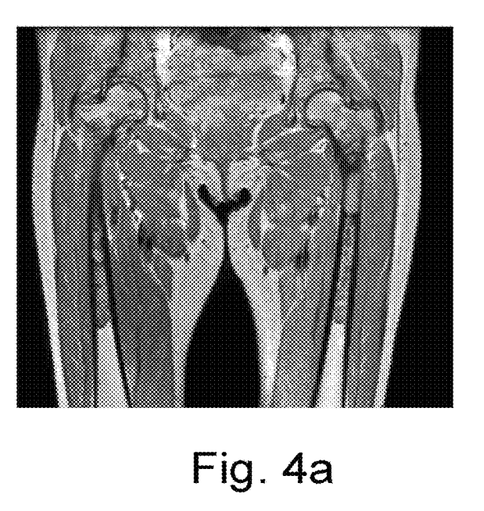
FIG. 4a is an MR image of a hip portion of a person.

FIGS. 1a, 2a and 3a are all sagittal MR images. FIG. 4a is a coronal MR image of a hip portion of a seventy-one years old female diagnosed with multiple myeloma (MM), a cancer of plasma cells.

Figure 4B:
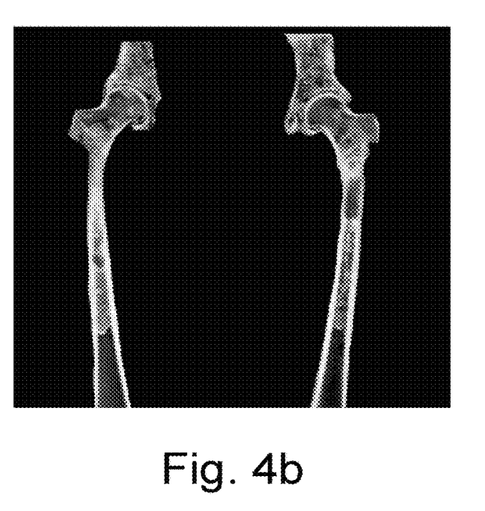
FIG. 4b is an image visualizing bone density.

FIG. 4b is the bone density image visualizing bone density of the hips of FIG. 4a, with the method described above. Abnormality within the hips can be visually detected in FIG. 4b. Thus, the estimated bone density and the bone density image can also serve as an alternative for preliminary screening for abnormality of the bones, which may facilitate early detection of diseases, such as multiple myeloma.

The imaged portion used in the examples may comprise bone portions of a human or an animal, such as a spinal bone, a hip bone, a leg bone, an ankle, a long bone, a wrist, a knee and a skull.

The invention claimed is:

1. A bone density estimating method, comprising:
   acquiring, by a magnetic resonance (MR) scanning device, an MR sequence of a body portion, wherein the MR sequence comprises quantitative information of the body portion;
   generating, by a processing circuit, an MR image of the body portion based on the MR sequence, wherein each voxel of the MR image represents a volume of the body portion;
   identifying, by the processing circuit, a part of the MR image representing a bone portion of the body portion; and
   for a voxel of the identified part of the MR image, estimating a bone density of a volume of the bone portion represented by the voxel, based on a quantitative value of the voxel;
   wherein the quantitative information of the body portion comprises a proton density.

2. The method of claim 1, wherein the step of estimating a bone density comprises:
   calculating a bone partial volume of the volume of the bone portion represented by the voxel, based on the quantitative value of the voxel;
   wherein the bone partial volume is a value represents a percentage of a bone tissue of a bone portion.

3. The method of claim 2, wherein the bone partial volume is calculated by a formula Bone Partial Volume=(100−(PD/$A$))%;

wherein PD is a proton density of the voxel,
   A is a first scaling factor, preferably in a range of 1.0 to 1.1.

4. The method of claim 3, comprising:
   calculating the first scaling factor A by a formula $A = B + C*R1$, or $A = B + C/T1$, wherein R1 is a longitudinal relaxation rate of the voxel, T1 is a longitudinal relaxation time of the voxel, and B and C are two constants such that the first scaling factor A is in a range of 1.0 to 1.4.

5. The method of claim 2, comprising:
   converting the calculated bone partial volume to a T-score value.

6. The method of claim 1, wherein the step of estimating a bone density comprises:
   calculating a T-score value of the volume of the bone portion represented by the voxel, based on the quantitative value of the voxel.

7. The method of claim 6, wherein the T-score value is calculated by a formula $T$-score value $= E - D*PD$ %;

wherein PD is a proton density of the voxel,
   D is a second scaling factor;
   E is an offset.

8. The method of claim 7, comprising:
   calculating the second scaling factor D by a formula $D = 16/(B + C*R1)$, or $D = 16/(B + C/T1)$, wherein R1 is a longitudinal relaxation rate of the voxel, T1 is a longitudinal relaxation time of the voxel, and B and C are two constants.

9. The method of claim 1, wherein the quantitative information of the body portion further comprises at least one of: a longitudinal relaxation rate R1, and a longitudinal relaxation time T1.

10. The method of claim 1, comprising:
    repeating the step of estimating a bone density for each voxel of the identified part of the MR image.

11. The method of claim 10, comprising:
    generating a bone density image for visualizing the estimated bone density for each voxel of the identified part of the MR image;
    wherein each voxel of the bone density image visualizes a bone density of its corresponding voxel of the identified part of the MR image; and
    wherein different bone densities are displayed differently in the bone density image.

12. The method of claim 11, comprising:
    displaying, by a user interface, the bone density image.

13. The method of claim 11, comprising:
    displaying the identified part of the MR image, the MR image or a different image representing an anatomy of the body portion or the bone portion as a background image; and
    displaying the bone density image as an overlay to the background image.

14. The method of claim 1, wherein the body portion comprises a plurality of vertebrae of a spine, and at least one vertebra of the plurality of vertebrae does not intersect a sagittal plane,
    the method further comprising:
    generating a partial sagittal MR image for each of the plurality of vertebrae based on the MR sequence; and
    combining partial sagittal MR images into a sagittal reformat MR image, as the MR image of the body portion based on the MR sequence;

wherein the plurality of vertebrae is visualized in the sagittal reformat MR image.

15. The method of claim 1, comprising:
calculating an average bone density of a region of interest of the identified part of the MR image.

16. The method of claim 15, comprising:
displaying the calculated average bone density value.

17. The method of claim 1, wherein the body portion comprises any of a spinal bone, a hip bone, a leg bone, an ankle, a long bone, a wrist, a knee and a skull.

18. The method of claim 1, wherein the step of identifying a part of the MR image comprises:
segmenting, by the processing circuit, the part of the MR image representing the bone portion.

19. A non-transitory computer readable recording medium having computer readable program code recorded thereon which when executed on a device having processing capability is configured to perform the method of claim 1.

20. A bone density estimating system, comprising:
a magnetic resonance (MR) scanning device, configured to acquire an MR sequence of a body portion, wherein the MR sequence comprises quantitative information of the body portion;
a processing circuit configured to:
generate an MR image of the body portion based on the MR sequence, wherein each voxel of the MR image represents a volume of the body portion;
identify a part of the MR image representing a bone portion of the body portion; and
for a voxel of the identified part of the MR image, estimate a bone density of a volume of the bone portion represented by the voxel, based on a quantitative value of the voxel;
wherein the quantitative information of the body portion comprises a proton density.

21. The system of claim 20, further comprising:
a user interface configured to display images.

* * * * *